United States Patent
Peng et al.

(10) Patent No.: US 11,506,600 B2
(45) Date of Patent: Nov. 22, 2022

(54) TERAHERTZ BIOLOGICAL DETECTION METHOD BASED ON FIVE-LEVEL RYDBERG QUANTUM STATE AND DEVICE COMPRISING SAME

(71) Applicant: University of Shanghai for Science and Technology, Shanghai (CN)

(72) Inventors: Yan Peng, Shanghai (CN); Yiming Zhu, Shanghai (CN); Ruijie Peng, Shanghai (CN); Yanchen Zhou, Shanghai (CN); Weinan Ge, Shanghai (CN); Jinbiao Zhang, Shanghai (CN); Songyan Hu, Shanghai (CN); Can Sun, Shanghai (CN); Li Zhou, Shanghai (CN); Xitian Hu, Shanghai (CN)

(73) Assignee: University of Shanghai for Science and Technology, Shanghai (CN)

( * ) Notice: Subject to any disclaimer, the term of this patent is extended or adjusted under 35 U.S.C. 154(b) by 27 days.

(21) Appl. No.: 17/321,668

(22) Filed: May 17, 2021

(65) Prior Publication Data
US 2021/0270731 A1    Sep. 2, 2021

(30) Foreign Application Priority Data

Jan. 21, 2021   (CN) .......................... 202110080273.1

(51) Int. Cl.
*G01N 21/3581*     (2014.01)
(52) U.S. Cl.
CPC . *G01N 21/3581* (2013.01); *G01N 2201/0636* (2013.01); *G01N 2201/06113* (2013.01)

(58) Field of Classification Search
CPC ..... G01N 21/3581; G01N 2201/06113; G01N 2201/0636; G01N 33/483; G01N 21/3586
See application file for complete search history.

(56) References Cited

U.S. PATENT DOCUMENTS

| | | | |
|---|---|---|---|
| 2016/0363617 A1* | 12/2016 | Anderson | G01R 29/0885 |
| 2019/0187198 A1* | 6/2019 | Anderson | G01R 29/0878 |
| 2021/0389248 A1* | 12/2021 | Wetherill | G01N 22/00 |
| 2022/0003829 A1* | 1/2022 | Anderson | G01S 3/781 |
| 2022/0196716 A1* | 6/2022 | Anderson | G01R 29/0892 |

FOREIGN PATENT DOCUMENTS

| | | |
|---|---|---|
| CN | 101498879 A | 8/2009 |
| CN | 110308108 A | 10/2019 |

* cited by examiner

*Primary Examiner* — Marcus H Taningco

(57) ABSTRACT

The present disclosure provides a terahertz biological detection method and a device comprising the same, in which biological samples with different molecular formulas have their characteristic peaks in the terahertz band. In the process of sweeping frequency with terahertz, when the terahertz frequency point corresponds to the characteristic peak frequency of the substance to be detected, resonant absorption occurs, and the transmitted/reflected terahertz wave electric field intensity will suddenly decrease. In the electromagnetically induced transparency spectrum corresponding to the Rydberg quantum state, the signal splitting amplitude is significantly reduced. Therefore, the characteristic peak frequency and specific content of the substance to be detected can be accurately determined by comparing the dependence of the Rydberg quantum state with the additional terahertz electric field intensity on the excitation energy level.

6 Claims, 3 Drawing Sheets

TERAHERTZ BIOLOGICAL DETECTION METHOD BASED ON FIVE-LEVEL RYDBERG QUANTUM STATE AND DEVICE COMPRISING SAME

CROSS-REFERENCE TO RELATED APPLICATIONS

This application claims the benefit of priority from Chinese Patent Application No. 202110080273.1, filed on Jan. 21, 2021. The content of the aforementioned application, including any intervening amendments thereto, is incorporated herein by reference in its entirety.

TECHNICAL FIELD

The present application relates to biological detection technologies, and more particularly to a terahertz biological detection method based on five-level Rydberg quantum state and a device comprising the same.

BACKGROUND

Terahertz is an electromagnetic wave with a frequency in the range of 0.1 THz to 10 THz, the band of which lies between microwave and infrared, and it has rich scientific significance and broad application prospects. The terahertz technology is characterized by its safety, where the energy of a terahertz photon is only millielectron volts, which will not damage the measured substance due to ionization. The Rydberg quantum state refers to an atom with highly excited electrons (the main quantum number n is very large). The Rydberg quantum state has a large polarizability $(n^*)^7$, and is extremely sensitive to the external field, so it is extremely easy to be manipulated by the external field.

The traditional terahertz time-domain spectroscopy system is limited by its low sensitivity, where the detection content of many key components in the sample can only be resolved to the milligram level, and the resolution accuracy is low. Therefore, the application range of terahertz waves in the field of biomedical testing is limited to a certain extent.

SUMMARY

Aiming at the problem of traditional terahertz detection of biological samples, the detection content of many key components contained in the sample only reaches the milligram level, and the accuracy is low, the present disclosure provides a terahertz biological detection method based on the five-level Rydberg quantum state and a device comprising the same, to realize a high-sensitivity, broad band, self-calibrated terahertz precision detection of biomedical samples at lower concentrations, which can be accurately calibrated to the international standard physical quantity (Planck constant). In addition, the system is more miniaturized, and the sample concentration is detected can reach the nanogram level.

The technical solutions of the disclosure are described as follows.

In a first aspect, the present disclosure provides a terahertz biological detection method based on five-level Rydberg quantum state, comprising:

(1) irradiating a plurality beams of laser lights on a same optical axis into a transparent vapor pool filled with metal atom vapors, so that atoms in the vapor pool are repeatedly transitioned from a ground state to a Rydberg state; detecting a light transmitted through a sample pool; displaying an electric signal on an oscilloscope after a purification for a detection signal;

(2) emitting, by a laser, a terahertz light into the vapor pool through a lens, so that the atoms in the vapor pool are transitioned to the five-level Rydberg state; detecting a light transmitted through the sample pool, and displaying the electric signal on the oscilloscope; wherein if a double peak split by EIT (Electromagnetically Induced Transparency) resonance appears AT (Autler-Townes) splitting, it is indicated that an additional terahertz wave field is detected;

(3) in a condition that a terahertz wave electric field in the vapor pool can be detected, adding a standard biological sample to be detected to a terahertz optical path and establishing a concentration gradient; sweeping a frequency by applying a terahertz frequency; observing an EIT-AT spectrum; establishing a terahertz frequency-EIT splitting interval curve graph, wherein an emergent characteristic peak is a characteristic peak of the detected standard biological sample; changing a sample concentration, wherein the higher a sample concentration, the stronger a light intensity absorption of the terahertz wave; sweeping the frequency by applying the terahertz frequency to obtain a terahertz frequency-EIT splitting interval curve diagram in a changed concentration; thereby establishing a reference diagram or a table of the EIT splitting interval corresponding to a composition, a concentration and a terahertz frequency of the standard biological sample; and (4) replacing the standard biological sample in the step (3) with a biological sample to be detected into the terahertz optical path; sweeping the frequency by applying the terahertz frequency; detecting the EIT-AT spectrum; comparing an obtained split interval and a corresponding terahertz frequency with the obtained reference graph or the table in the step (3), to obtain a composition and a concentration of the biological sample to be detected.

In some embodiments, in the step (4), the minimum detection concentration accuracy of components of the biological sample to be detected reaches a nanogram level.

In a second aspect, the present disclosure provides a terahertz biological detection device for operating the terahertz biological detection method based on five-level Rydberg quantum state of claim 1, comprising:

three excitation lasers, comprising a first excitation laser, a second excitation laser, and a third excitation laser;
a terahertz generator;
an optical device;
a vapor pool filled with metal atoms; and
a detector arranged below the vapor pool for detecting the vapor pool;

wherein a laser light emitted by the first excitation laser hits the vapor pool directly; a laser light emitted by the second excitation laser and a laser light emitted by the third excitation laser are reflected and transmitted by a first reflector and hit a beam splitter together; each of the laser lights emitted by the second excitation laser and the third excitation laser is divided into two beams of light through the beam splitter, one beam of transmitted light hits the vapor pool, and the other beam of reflected light hits a second reflector and is reflected to hit a reference light detector to be detected; a center wavelength emitted by the first excitation laser resonates with a ground state and a first excited state transition of the atoms in the vapor pool; the laser light emitted by the second excitation laser and the laser light emitted by the third excitation laser make the atoms transition from the first excited state to the second excited state, and then transition to the Rydberg state after reaching the second excited state; terahertz lights emitted by the terahertz generator respectively hit the vapor pool through a lens in turn; the detector and the reference light detector are connected to an oscilloscope together.

In some embodiments, the biological sample to be detected is placed in an optical path between the lens and the vapor pool.

In some embodiments, the metal atoms in the transparent vapor pool and wavelength parameters of the three excitation lasers are coordinated to adjust to obtain the Rydberg state in the transparent vapor pool.

In some embodiments, the first reflector is a dichroic mirror configured to reflect a light having a wavelength same as an output of the second excitation laser and transmit a light having a wavelength same as an output of the third excitation laser.

Compared to the prior art, the present disclosure has the following beneficial effects.

In the terahertz biological detection method based on five-level Rydberg quantum state and a device comprising the same provided in the present disclosure, the measurement of an amplitude of terahertz light passing through a biological sample is transformed into a measurement of frequency through an EIT technology, to realize a high sensitivity, broad band, self-calibration precision detection at the nanogram level for the biomedical samples, which can be accurately calibrated to the international standard physical quantity (Planck constant). In addition, the system is more miniaturized, to apply to a wide range and various types of samples.

DETAILED DESCRIPTION OF EMBODIMENTS

The present disclosure will be described in detail below with reference to the drawings and specific embodiments. These embodiments are implemented on the premise of the technical solution of the present disclosure, where detailed implementation and specific operation procedures are provided, but the protection scope of the present disclosure is not limited to the following embodiments.

Figure 1:
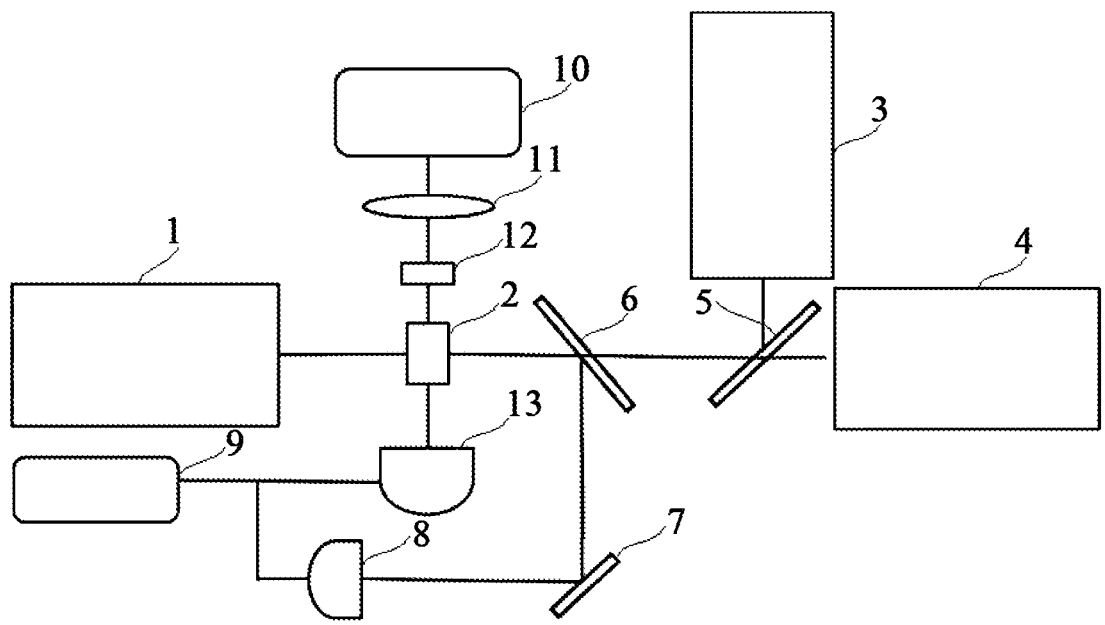
FIG. 1 is a schematic diagram of a terahertz biological detection device based on a five-level Rydberg quantum state according to an embodiment of the present disclosure.

As shown in FIG. 1, provided is a terahertz biological detection device based on a five-level Rydberg quantum state, including four excitation lasers (including a first excitation laser 1, a second excitation laser 3, a third excitation laser 4, and a fourth excitation laser 10), an optical device, a vapor pool 2 filled with metal atoms, and a first detector 13 arranged below the vapor pool 2 for detecting the vapor pool 2. A laser light emitted by the first excitation laser 1 hits the vapor pool 2 directly. A laser light emitted by the second excitation laser 3 and a laser light emitted by the third excitation laser 4 are reflected and transmitted by a first reflector 5 and hit a beam splitter 6 together. Each laser is divided into two beams by the beam splitter 6, one beam of transmitted light hits the vapor pool 2, and the other beam of reflected light hits a second reflector 7 and then hits a second detector 8 to be detected. The terahertz light emitted by the fourth excitation laser 10 passes through the lens 11 and the biological sample 12 respectively and then hits the vapor pool 2. The first detector 13 and the second detector 8 are connected to the oscilloscope 9. The oscilloscope 9 can ensure that the beam signal is accurately reflected and presented. A center wavelength emitted by the first excitation laser 1 resonates with the ground state and a first excited state transition of the atoms in the vapor pool 2. The laser light emitted by the second excitation laser 3 and the laser light emitted by the second excitation laser 4 make the atoms transition from the first excited state to the second excited state, and then transition to the Rydberg state after reaching the second excited state.

The vapor pool 2 is filled with cesium atom vapor at a saturated vapor pressure. The first excitation laser 1 emits a laser light with a center wavelength of 852 nm, and wavelengths of the laser lights emitted by the excitation laser 3 are respectively 1470 nm and 800 nm. The parameters of the cesium atom and the wavelengths of the three excitation lasers 1, 3, and 4 can all be coordinated according to actual use.

The first reflector 5 is a dichroic mirror configured to reflect a light having a wavelength of 1470 nm and transmit a light having a wavelength of 800 nm.

The present disclosure further provides a terahertz biological detection method based on five-level Rydberg quantum state, including the following steps.

(1) Three beams of laser lights (the wavelengths thereof can reach nanometer level) on a same optical axis are irradiated into a transparent vapor pool filled with cesium metal atom vapors to prepare the five-level Rydberg quantum state. The first beam of laser light (emitted by the first excitation laser 1) transitions the atoms in the vapor pool from the ground state to the first excited state. The second beam of laser light (emitted by the second excitation laser 3) transitions the atoms from the first excited state to the second excited state, and the third beam of laser light (emitted by the third excitation laser 4) transitions the atoms from the second excited state to a specific Rydberg state. The lights transmitted through the vapor pool whose frequencies are not the same as that of the detecting light (the light emitted by laser 1 is the detecting light, and its frequency is 852 nm, which can be set directly by laser 1) are filtered out, and the remaining detecting light signal are collected and converted to the corresponding electrical signal.

(2) The fourth excitation laser 10 emits a terahertz light through the lens 11 and hits the vapor pool 2. Due to an additional terahertz field, the atoms are transitioned to the five-level Rydberg state. At this time, there is an additional terahertz wave field (emitted by the fourth excitation laser 10) at the position of the sample vapor pool, and the electrical signal is sent by the first detector 13 and displayed on the oscilloscope 9. If the electrical signal interface appears split double peaks, it is indicated that the EIT (Electromagnetically Induced Transparency) resonance splits into two, and an AT (Autler-Townes) split phenomenon is appeared.

Figure 2A:
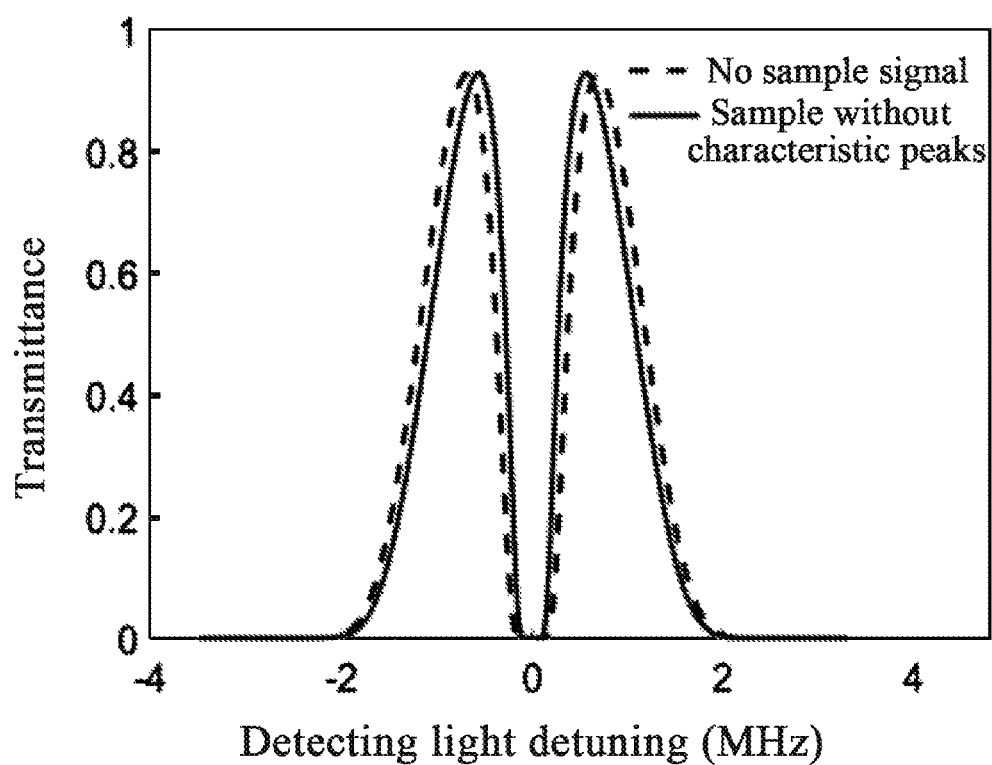
FIG. 2a is a comparison diagram of a detecting light before and after adding a sample without characteristic peaks to a method of present disclosure.
Figure 2B:
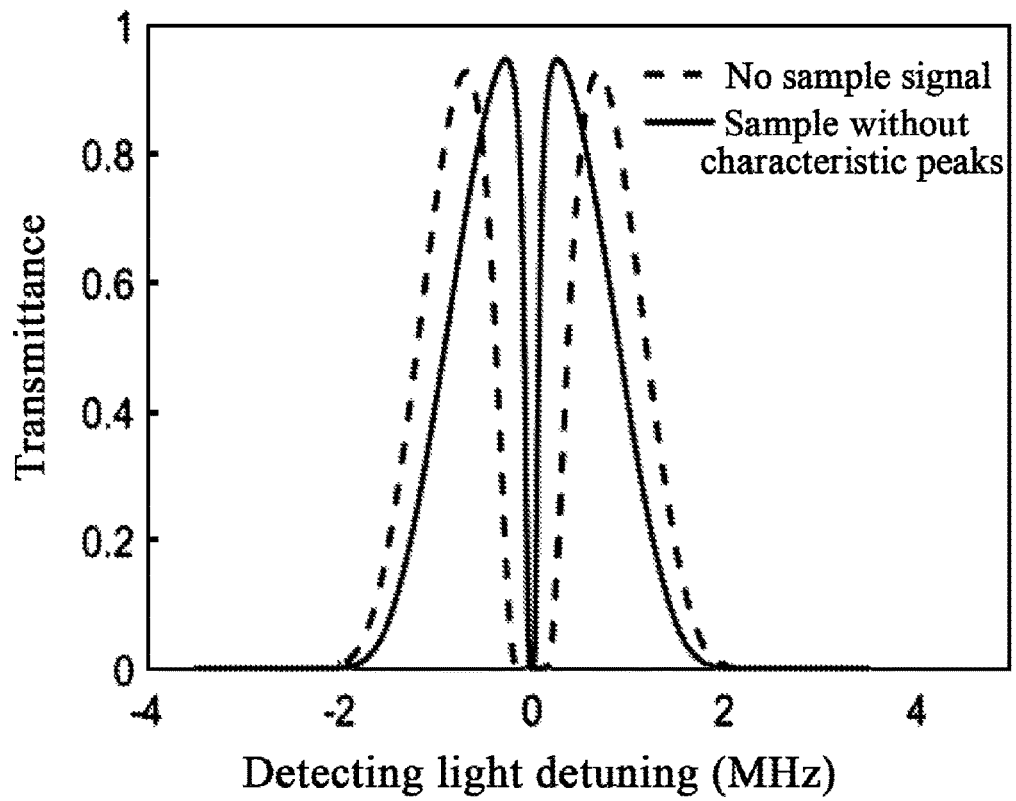
FIG. 2b is a comparison diagram of a detecting light before and after adding a sample with characteristic peaks to the method of present disclosure.
Figure 2C:
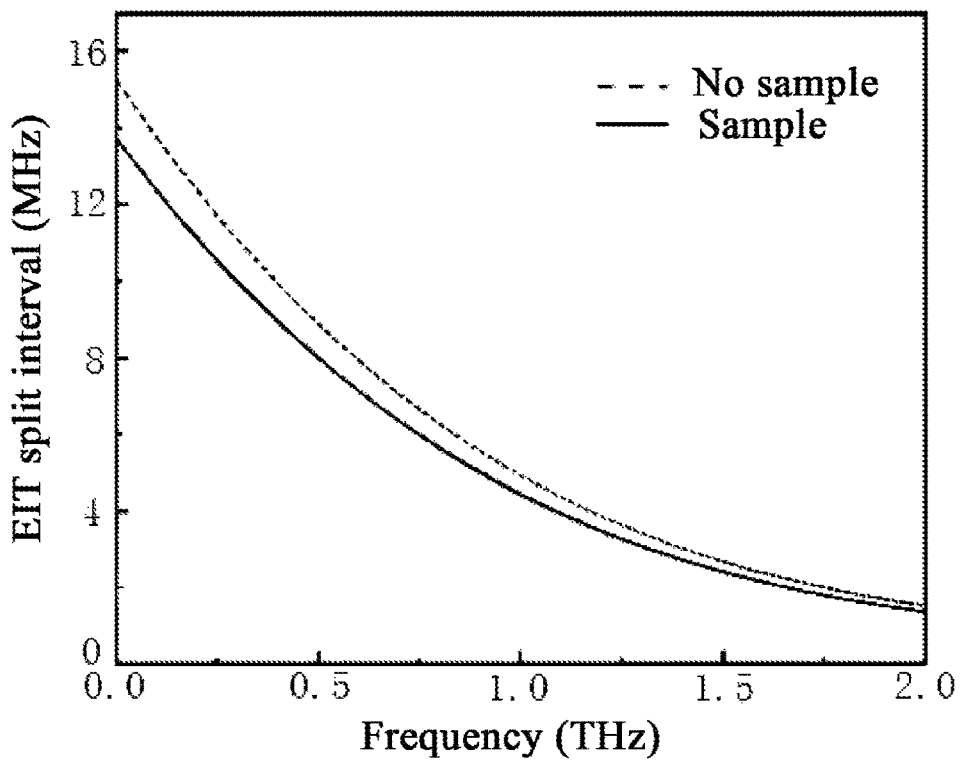
FIG. 2c is a comparison diagram of an EIT splitting interval before and after adding the sample without characteristic peaks to the method of present disclosure, while performing a frequency sweep with terahertz frequency.
Figure 2D:
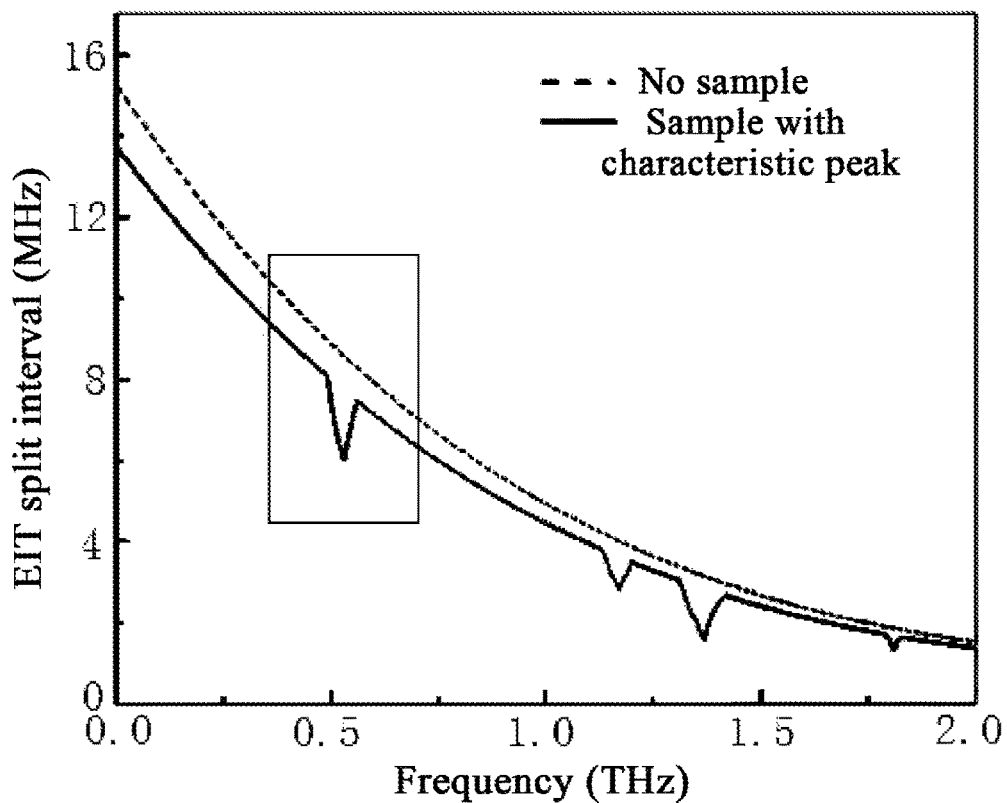
FIG. 2d is a comparison diagram of an EIT splitting interval before and after adding the sample with characteristic peaks to the method of present disclosure, while performing the frequency sweep with terahertz frequency.
Figure 2E:
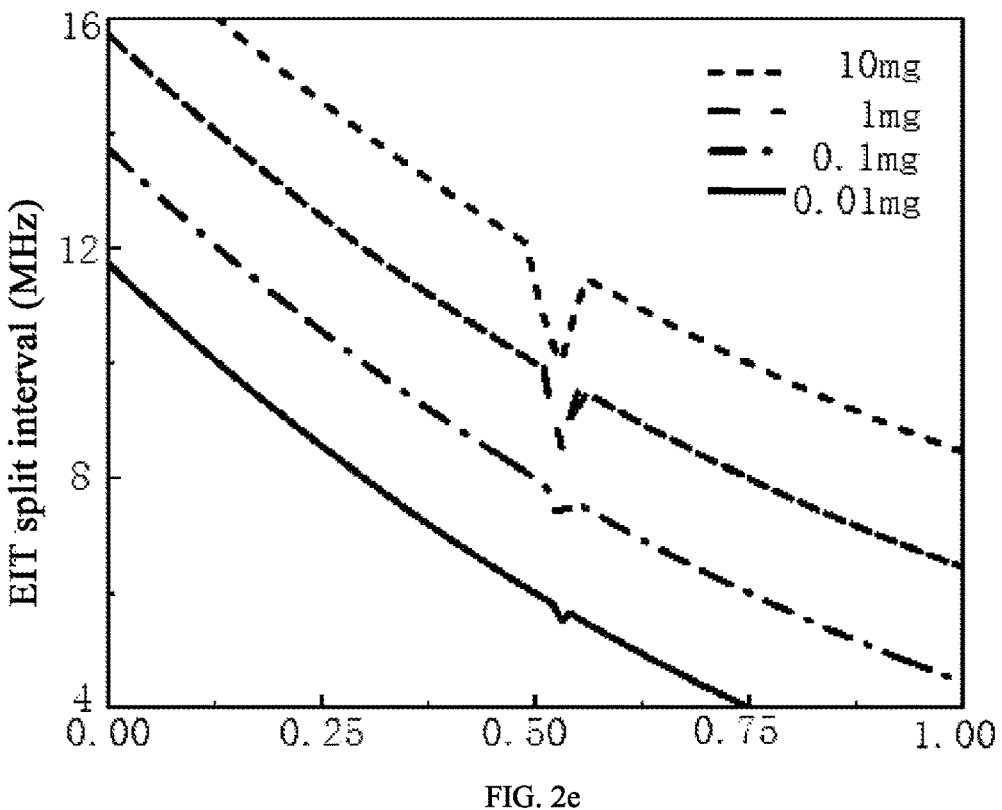
FIG. 2e is a partial enlarged view of a characteristic peak part in a frame line of FIG. 2d detected at different concentrations.

(3) The split signal indicates that the device has detected the terahertz electric field applied at this time. At this time, the biological sample 12 to be detected is added to the terahertz optical path and a concentration gradient is established. The EIT-AT spectrum is observed. If the biological sample is a sample without characteristic peaks, the EIT splitting interval will be slightly smaller (after the normal loss of the sample), and the degree of reduction is not obvious, as shown in FIG. 2a. If the biological sample is a sample with characteristic peaks, the EIT splitting interval will be significantly reduced, as shown in FIG. 2b. This is because when the sample responds to the terahertz with a specific frequency, part of the terahertz light is absorbed by the sample, the signal intensity becomes smaller, the EIT spectrum becomes smaller, and the split width becomes smaller. The sample concentration is changed, as shown in FIG. 2e. The higher the sample concentration, the stronger the absorption of THz light intensity and the smaller the spectral splitting interval. Therefore, the components contained in the sample can be estimated by comparing the degree of peak change before and after adding the biological sample.

(4) The frequency is swept by applying the terahertz frequency to enable Rydberg quantum state to detect the terahertz broadband signal, and the splitting of the electrical signal can be displayed by the second detector 8 and the first detector 13 (the second detector 8 is to determine the three wavelengths of the three excitation lasers 1, 3, 4, although the three excitation lasers can be directly set to the required wavelength range, the setting wavelength is different from the actual wavelength, so the second detector 8 is needed to confirm; and the first detector 13 is configured to detect the EIT split signal). The change of the EIT-AT spectrum is observed, and the position of the characteristic peak of the sample is determined, so that the composition of the sample is inferred. According to FIGS. 2a and 2b, combined with the principle that as the terahertz frequency increases, the EIT splitting gradually decreases, it can be concluded that the EIT splitting interval of the sample without characteristic peaks decreases with an increase of THz, as shown in FIG. 2c. As shown in FIG. 2d, the EIT splitting interval of the sample with characteristic peaks generally maintains a tendency to decrease with the increase of THz, but its interval suddenly decreases at several corresponding THz frequency points. It can be seen that the sample has a total of four characteristic peaks, and the components contained in the sample can be determined from the terahertz frequency at which the characteristic peaks are located.

(5) The EIT split signal diagram of the standard concentration biological sample to be detected is adopted as a standard, and the EIT diagrams of different concentrations of each sample measured in the step (3) and the step (4) is compared to distinguish a component and a concentration of the sample to be detected. The higher the sample concentration, the stronger the absorption of THz light intensity and the smaller the spectral splitting interval. The accuracy of detecting the concentration of sample components can reach the nanograms level. As shown in FIG. 2e, provided is a partial enlarged view of a characteristic peak part in a frame line of FIG. 2d detected at different concentrations, which cannot be achieved in the existing various terahertz devices and methods (a lower limit of detectable concentration is at the nanogram level).

Described above are only the embodiments of the present disclosure and the technical principles of application. The present disclosure is not limited to the specific embodiments described herein, and various obvious changes, readjustments and substitutions can be made to those skilled in the art without departing from the protection scope of the present disclosure. Therefore, although the present disclosure has been described through the above embodiments, it is not limited to the above embodiments. Without departing from the concept of the present disclosure, it can also include more other equivalent embodiments, which are not limited to these embodiments.

What is claimed is:

1. A terahertz biological detection method based on five-level Rydberg quantum state, comprising:
    (1) irradiating a plurality beams of laser lights on a same optical axis into a transparent vapor pool filled with metal atom vapors, so that atoms in the vapor pool are repeatedly transitioned from a ground state to a Rydberg state; detecting a light transmitted through a sample pool; displaying an electric signal on an oscilloscope after a purification for a detection signal;
    (2) emitting, by a laser, a terahertz light into the vapor pool through a lens, so that the atoms in the vapor pool are transitioned to the five-level Rydberg state; detecting a light transmitted through the sample pool, and displaying the electric signal on the oscilloscope; wherein if a double peak split by EIT (Electromagnetically Induced Transparency) resonance appears AT (Autler-Townes) splitting, it is indicated that an additional terahertz wave field is detected;
    (3) in a condition that a terahertz wave electric field in the vapor pool can be detected, adding a standard biological sample to be detected to a terahertz optical path and establishing a concentration gradient; sweeping a frequency by applying a terahertz frequency; observing an EIT-AT spectrum; establishing a terahertz frequency-EIT splitting interval curve graph, wherein an emergent characteristic peak is a characteristic peak of the detected standard biological sample; changing a sample concentration, wherein the higher a sample concentration, the stronger a light intensity absorption of the terahertz wave; sweeping the frequency by applying the terahertz frequency to obtain a terahertz frequency-EIT splitting interval curve diagram in a changed concentration; thereby establishing a reference diagram or a table of the EIT splitting interval corresponding to a composition, a concentration and a terahertz frequency of the standard biological sample; and
    (4) replacing the standard biological sample in the step (3) with a biological sample to be detected into the terahertz optical path; sweeping the frequency by applying the terahertz frequency; detecting the EIT-AT spectrum; comparing an obtained split interval and a corresponding terahertz frequency with the obtained reference graph or the table in the step (3), to obtain a composition and a concentration of the biological sample to be detected.

2. The terahertz biological detection method of claim 1, wherein in the step (4), the minimum detection concentration accuracy of components of the biological sample to be detected reaches a nanogram level.

3. A terahertz biological detection device for operating the terahertz biological detection method based on five-level Rydberg quantum state of claim 1, comprising:
    three excitation lasers, comprising a first excitation laser, a second excitation laser, and a third excitation laser;

a terahertz generator;
an optical device;
a vapor pool filled with metal atoms; and
a detector arranged below the vapor pool for detecting the vapor pool;
wherein a laser light emitted by the first excitation laser hits the vapor pool directly; a laser light emitted by the second excitation laser and a laser light emitted by the third excitation laser are reflected and transmitted by a first reflector and hit a beam splitter together; each of the laser lights emitted by the second excitation laser and the third excitation laser is divided into two beams of light through the beam splitter, one beam of transmitted light hits the vapor pool, and the other beam of reflected light hits a second reflector and is reflected to hit a reference light detector to be detected; a center wavelength emitted by the first excitation laser resonates with a ground state and a first excited state transition of the atoms in the vapor pool; the laser light emitted by the second excitation laser and the laser light emitted by the third excitation laser make the atoms transition from the first excited state to the second excited state, and then transition to the Rydberg state after reaching the second excited state; terahertz lights emitted by the terahertz generator respectively hit the vapor pool through a lens in turn; the detector and the reference light detector are connected to an oscilloscope together.

4. The detection device of claim 3, wherein the biological sample to be detected is placed in an optical path between the lens and the vapor pool.

5. The detection device of claim 4, wherein the metal atoms in the transparent vapor pool and wavelength parameters of the three excitation lasers are coordinated to adjust to obtain the Rydberg state in the transparent vapor pool.

6. The detection device of claim 5, wherein the first reflector is a dichroic mirror configured to reflect a light having a wavelength same as an output of the second excitation laser and transmit a light having a wavelength same as an output of the third excitation laser.

* * * * *